March 1, 1955 F. MEILLAND Plant Pat. 1,358
ROSE PLANT
Filed May 26, 1954
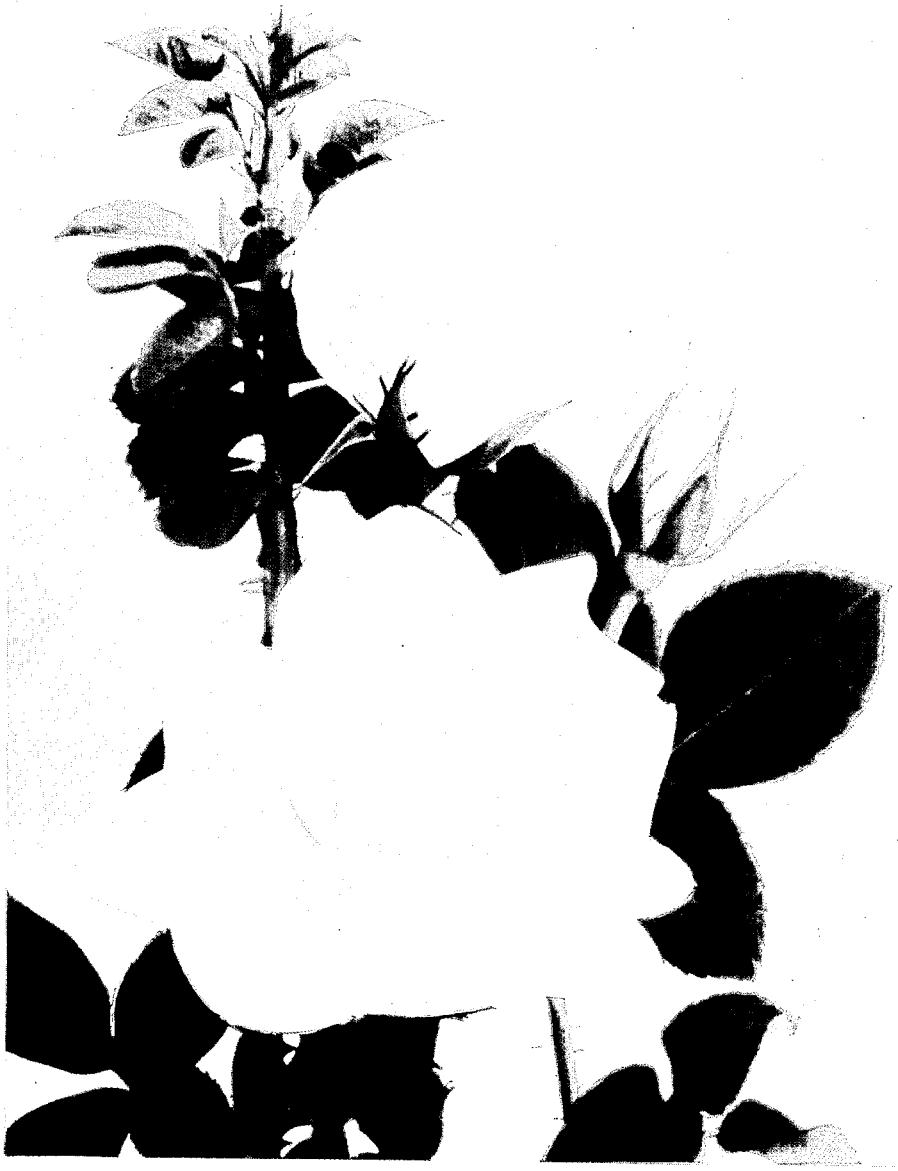
Inventor.
Francis Meilland
By: Robert Cobb
Attorneys.

United States Patent Office

Plant Pat. 1,358

Patented Mar. 1, 1955

1,358

ROSE PLANT

Francis Meilland, Cap Azura, Cap d'Antibes, France, assignor to The Conard-Pyle Company, West Grove, Pa., a corporation of Pennsylvania Application May 26, 1954, Serial No. 432,626

Claims priority, application France July 7, 1953

1 Claim. (Cl. 47—61)

The present invention relates to a new and distinct variety of rose plant of the hybrid tea class, which was originated by me by crossing the variety "Peace" (Plant Patent No. 591) with the variety "Europa" (unpatented).

The primary objective in making this cross was to produce a new variety which combines certain desirable characteristics of both parent varieties and which, in combination, represent a marked difference from both parents, as well as from all other varieties of the hybrid tea class. This objective was fully achieved, as evidenced by the combination in my new variety of a strong and vigorous habit of plant growth, with heavy canes, and the very large and well-formed blooms which are particularly characterized by an unusual permanence of their pink general color tonality from the bud to the fully open bloom stage, remaining substantially unchanged throughout the blooming season. This latter feature is quite unusual in pink roses, and being combined with the large size of the blooms, which average from 5 inches to 5½ inches in diameter, and which are fully double, makes my new variety especially attractive and different from any prior pink roses of which I am aware. Besides the desirable vigorous habit of growth of the plants of my new variety, the plants are upright, well-branched and stocky, and their freedom of bloom further contributes to the superior qualities of my new variety which are not duplicated in any other pink variety.

Asexual reproduction of my new variety by budding in France, as well as at West Grove, Pennsylvania, U. S. A., shows that the foregoing characteristics and distinctions come true to form and are established and transmitted through succeeding propagations.

The accompanying drawing shows typical specimens of the foliage, stems and blooms of my new variety in different stages of development and as depicted in color as nearly true as it is reasonably possible to make the same in a color illustration of this character.

The following is a detailed description of the new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Peace."
*Pollen parent.*—"Europa."
Propagation: Holds its distinguishing characteristics through succeeding propagations by budding.

FLOWER

Locality where grown and observed: West Grove, Pennsylvania, U. S. A.
Flowers borne: Singly; on medium length stems of normal strength.
Quantity of bloom: Free, both outdoors and in greenhouse.
Continuity: Continuous.
Fragrance: Moderate. Nature—tea.
Bud:
*Peduncle.*—Medium length; medium caliper; erect; rough; with medium number of green prickles. Color—Lettuce Green, Plate V.

*Before calyx breaks.*—Size—medium. Form—medium length; pointed; with a conspicuous neck; with foliaceous appendages on the surface of the bud; with medium stout, little-cut, bristle-like foliaceous parts extending beyond the tip of the bud equal to ½ of more of its length.
*As calyx breaks.*—Color—Acajou Red, Plate XIII.
*As first petal opens.*—Size—medium. Form—long; ovoid. Color: Outside—Eosine Pink, Plate I, shading gradually into Begonia Rose, Plate I; where exposed to sunlight, color is Thulite Pink, Plate XXVI. Inside—Deep Rose Pink, Plate XII, with margin of Old Rose, Plate XIII at base, and with base of Light Greenish Yellow, Plate V.
*Opening.*—Opens up well.
Bloom:
*Size (when fully open).*—Large; from 5 inches to 5½ inches in diameter.
*Petalage.*—Double; from 50 to 65 petals; arranged regularly.
*Form.*—Cupped, at first; becoming shallow-cupped; petals being at first loosely rolled outward, and remaining loosely rolled outward at maturity.
Petals: Medium thickness; with inside satiny and outside satiny. Shape: Outer petals—Broadly obovate; scalloped; with apex flat; with 1 notch. Intermediate petals—almost round; with 1 notch. Inner petals—round; irregular; usually with 1 notch.

This description of a newly opened flower was made from a rose grown in a greenhouse in the month of March, at West Grove, Pennsylvania, U. S. A.:

*Color.*—Outer petal: Outside surface—Deep Rose Pink, Plate XII, veined with Rose Pink, Plate XII; point of attachment is clear Dull Green Yellow, Plate XVII. Inside surface—between Rose Pink, Plate XII and Deep Rose Pink, Plate XII, with margin Deep Rose Pink, Plate XII; point of attachment is Greenish Yellow, Plate V; midrib of petal sometimes lined with green. Intermediate petal: Outside surface—Deep Rose Pink, Plate XII; point of attachment is Wax Yellow, Plate XVI. Inside surface—between Deep Rose Pink, Plate XII and Rose Color, Plate XII, with base of petal Strawberry Pink, Plate I; point of attachment is Empire Yellow, Plate IV. Inner petal: Outside surface—Deep Rose Pink, Plate XII, usually veined with dull white along the midrib; point of attachment is Empire Yellow, Plate IV. Inside surface—between Deep Rose Pink, Plate XII and Rose Color, Plate XII; point of attachment is Wax Yellow, Plate XVI, and is surrounded by aura of Light Orange Yellow, Plate III.

This description was made from a rose that was open for three days in a greenhouse in the month of March, at West Grove, Pennsylvania, U. S. A.:

*Color.*—Outer petal: Outside surface—Deep Rose Pink, Plate XII, with veins of Rose Color, Plate XII, and base of Light Buff, Plate XV. Inside surface—Spinel Pink, Plate XXVI, shading to Light Viridine Yellow, Plate V at base. Inner petal: Outside surface—Deep Rose Pink, Plate XII; lower margin of some petals shows Light Jasper Red, Plate XIII. Inside surface—Deep Rose Pink, Plate XII, sometimes showing Light Jasper Red, Plate XIII; area surrounding point of attachment is Wax Yellow, Plate XVI.
*General color effect.*—Newly opened flower—an even Deep Rose Pink, Plate XII. 3-days open—Spinel Pink, Plate XXVI.
*Behavior.*—Drop off cleanly.
*Flower longevity.*—On bush in garden—5 days in month of June. Cut roses grown outdoors and kept at living-room temperatures—4 days in month of June. Cut roses grown in greenhouse and kept at living room temperatures—3 days in month of March.

REPRODUCTIVE ORGANS

Stamens. Many; arranged irregularly about pistils; mixed with petaloids.
Filaments: Many; most with anthers; medium length. Color—Carmine, Plate I.
Anthers: Open at various times; medium size. Color—Light Cadmium, Plate IV.
Pollen: Moderate. Color—gold.
Pistils: Medium number.
Styles: Uneven; medium length; thin; loosely bunched.
Stigma: Color—pale yellow.
Ovaries: All enclosed in calyx.
Hips: Short; globular; with inconspicuous neck; smooth; thick walls. Color—russet brown.
Sepals: Permanent; moderately long; spear-shaped.
Seeds: Medium number; medium size.

PLANT

Foliage:

*Leaves.*—Usually compound of 5, but occasionally 3 or 7, leaflets: normal abundance; medium size; moderately thin.

*Leaflets.*—Shape—broadly oval; base round; margin simply serrate.

*Color.*—Mature: upper surface—Forest Green, Plate XVII; under surface—between Light Bice Green, Plate XVII and Bice Green, Plate XVII. Young: upper surface—Parrot Green, Plate VI; under surface—overall effect is Deep Vinaceous, Plate XXVII.

*Rachis (the supporting stem of the compound leaf).*—Medium caliper. Upper side—grooved; hairy; prickly along upper edges. Under side—moderately thorny.

*Stipules.*—Medium length; moderately narrow; with medium length points turning out at an angle of less than 45°.

*Disease resistance.*—Good resistance to mildew and blackspot, and not usually susceptible to rust, as compared with other varieties grown under comparable cultural conditions at West Grove, Pennsylvania, U. S. A., and in France.

*Frost resistance.*—Excellent, as compared with other varieties grown under comparable cultural conditions at West Grove, Pennsylvania, U. S. A., and in France.

Growth:

*Habit.*—Bushy; much-branched.

*Growth.*—Free.

*Canes.*—Medium heavy.

*Main stems.*—Color—Light Hellebore Green, Plate XVII. Thorns—several; medium length; pointed slightly downward; with medium length, broad, oval base. Prickles—several. Color—green. Hairs—none.

*Branches.*—Color—Light Bice Green, Plate XVII. Thorns—several; medium length; pointed slightly downward; with medium length, narrow, oval base. Prickles—several. Color—green. Hairs—none.

*New shoots.*—Color—bright green. Thorns—several; medium length; pointed downward; with medium length, narrow, oval base. Prickles—few. Color—reddish. Hairs—none.

I claim:

A new and distinct variety of rose plant of the hybrid tea class, substantially as herein shown and described, characterized particularly as to novelty by the combination of the unusual permanence of the pink general color tonality of its blooms from the bud to the fully open bloom stage and remaining substantially unchanged throughout the blooming season, the relatively large and above-average size of the blooms, the fully double form of the blooms, the strong, vigorous, upright, well-branched and stocky habits of growth of the plant, and the freedom of bloom thereof.

No references cited.